(12) United States Patent
Choi et al.

(10) Patent No.: US 12,239,425 B2
(45) Date of Patent: Mar. 4, 2025

(54) APPARATUS AND METHOD FOR ESTIMATING BLOOD PRESSURE

(71) Applicant: SAMSUNG ELECTRONICS CO., LTD., Suwon-si (KR)

(72) Inventors: Jin Woo Choi, Suwon-si (KR); Jae Min Kang, Seoul (KR); Seung Woo Noh, Seongnam-si (KR); Sang Yun Park, Hwaseong-si (KR); Hye Rim Lim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 619 days.

(21) Appl. No.: 17/373,015

(22) Filed: Jul. 12, 2021

(65) Prior Publication Data

US 2022/0296114 A1    Sep. 22, 2022

(30) Foreign Application Priority Data

Mar. 19, 2021    (KR) ........................ 10-2021-0035740

(51) Int. Cl.
*A61B 5/022* (2006.01)
*A61B 5/00* (2006.01)
(Continued)

(52) U.S. Cl.
CPC ...... *A61B 5/02225* (2013.01); *A61B 5/02108* (2013.01); *A61B 5/7275* (2013.01);
(Continued)

(58) Field of Classification Search
CPC ........ A61B 2562/0247; A61B 5/02416; A61B 5/681–6815; A61B 5/6843;
(Continued)

(56) References Cited

U.S. PATENT DOCUMENTS 10,398,324 B2    9/2019    Mukkamala et al.
11,419,562 B2    8/2022    Kang et al.
(Continued)

FOREIGN PATENT DOCUMENTS

JP    2016-220886 A    12/2016
KR    10-2006-0081178 A    7/2006
(Continued)

OTHER PUBLICATIONS

Chandrasekhar; "Formulas to Explain Popular Oscillometric Blood Pressure Estimation Algorithms"; Nov. 21, 2019; Front. Physiol. 10:1415 (Year: 2019).*

(Continued)

*Primary Examiner* — Colin T. Sakamoto
*Assistant Examiner* — Andrew W Begeman
(74) *Attorney, Agent, or Firm* — Sughrue Mion, PLLC

(57) ABSTRACT

An apparatus for estimating blood pressure is provided. According to one embodiment, the apparatus for estimating blood pressure may include: a first sensor configured to obtain a pulse wave signal of a green wavelength from an object when the object is in contact with the first sensor; a second sensor configured to measure an external force applied to the second sensor while the first sensor is obtaining the pulse wave signal; and a processor configured to obtain an oscillometric envelope based on a direct current (DC) component of the pulse wave signal of the green wavelength and the external force, and estimate the blood pressure using the oscillometric envelope.

12 Claims, 15 Drawing Sheets

(51) Int. Cl.
*A61B 5/021* (2006.01)
*A61B 5/024* (2006.01)

(52) U.S. Cl.
CPC .......... *A61B 5/02416* (2013.01); *A61B 5/681* (2013.01); *A61B 5/6815* (2013.01); *A61B 5/6898* (2013.01); *A61B 2562/0247* (2013.01)

(58) Field of Classification Search
CPC ........ A61B 5/6898; A61B 5/725–7275; A61B 5/021–02141; A61B 5/022–0235; A61B 5/02225
See application file for complete search history.

(56) References Cited

U.S. PATENT DOCUMENTS

| | | | |
|---|---|---|---|
| 11,478,157 | B2 | 10/2022 | Kwon et al. |
| 2003/0135124 | A1 | 7/2003 | Russell |
| 2011/0105917 | A1 | 5/2011 | Fortin et al. |
| 2016/0310084 | A1 | 10/2016 | Banerjee et al. |
| 2018/0185643 | A1 | 7/2018 | Lee et al. |
| 2019/0110758 | A1 | 4/2019 | Kang et al. |
| 2019/0125198 | A1* | 5/2019 | Kang ................ A61B 5/02427 |
| 2020/0037956 | A1* | 2/2020 | Kang ................ G06V 40/1306 |
| 2020/0146565 | A1 | 5/2020 | Park et al. |
| 2020/0367760 | A1 | 11/2020 | Klaassen et al. |

FOREIGN PATENT DOCUMENTS

| | | |
|---|---|---|
| KR | 10-2019-0043464 A | 4/2019 |
| KR | 10-2019-0105421 A | 9/2019 |
| KR | 10-2019-0119414 A | 10/2019 |
| KR | 10-2020-0001911 A | 1/2020 |
| KR | 10-2020-0034422 A | 3/2020 |
| KR | 10-2020-0055313 A | 5/2020 |

OTHER PUBLICATIONS

Lubin; "Blood pressure measurement by coupling an external pressure and photo-plethysmographic signals"; IEEE; 2020 ; 2020 42nd Annual International Conference of the IEEE EMBC; pp. 4996-4999; (Year: 2020).*
Communication dated Oct. 31, 2022 issued by the Korean Patent Office in Korean Patent Application No. 10-2021-0035740.
Remo Lazazzera et al., "A New Wearable Device for Blood Pressure Estimation Using Photoplethysmogram", Sensors, Jun. 4, 2019, vol. 19, No. 2557, pp. 1-18 (18 pages total).

* cited by examiner

APPARATUS AND METHOD FOR ESTIMATING BLOOD PRESSURE

CROSS-REFERENCE TO RELATED APPLICATION(S)

This application claims priority from Korean Patent Application No. 10-2021-0035740, filed on Mar. 19, 2021, in the Korean Intellectual Property Office, the disclosure of which is incorporated herein by reference in its entirety.

BACKGROUND

1. Field

Apparatuses and methods consistent with example embodiments relate to estimating blood pressure, and more particularly, to a cuff-less blood pressure measurement based on oscillometry.

2. Description of Related Art

General techniques for non-invasive extraction of cardiovascular features without the use of a compression cuff include pulse wave analysis and pulse wave velocity measurement.

The pulse wave analysis is a method of extracting cardiovascular characteristics by analyzing the shape of a photoplethysmography (PPG) or a body surface pressure signal obtained from a body distal end, such as a fingertip, a radial artery, or the like. Blood ejected from the left ventricle causes reflection at the sites of large branches, such as the renal arteries and the lower aorta, which affects the shape of the PPG or a body surface pressure wave measured at the body distal end. Accordingly, by analyzing the shape of the pulse wave, it is possible to estimate a degree of arteriosclerosis, vascular age, aortic pressure waveform, or the like.

The pulse wave velocity measurement is a method of extracting cardiovascular characteristics, such as a degree of arteriosclerosis, blood pressure, or the like, by measuring a pulse wave propagation time, wherein a pulse transit time (PTT) between an R peak (left ventricular contraction interval) of an electrocardiogram (ECG) and a peak of a PPG is measured by measuring the ECG and the PPG at the body distal end and a velocity at which the blood from the heart reaches the body distal end is calculated by dividing an approximate length of an arm by the measurement result.

SUMMARY

Example embodiments address at least the above problems and/or disadvantages and other disadvantages not described above. Also, the example embodiments are not required to overcome the disadvantages described above, and may not overcome any of the problems described above.

According to an aspect of an example embodiment, there is provided an apparatus for estimating blood pressure, including: a first sensor configured to obtain a pulse wave signal of a green wavelength from an object when the object is in contact with the first sensor; a second sensor configured to measure an external force applied to the second sensor while the first sensor is obtaining the pulse wave signal; and a processor configured to obtain an oscillometric envelope based on a direct current (DC) component of the pulse wave signal of the green wavelength and the external force, and estimate the blood pressure using the oscillometric envelope.

The first sensor may include a light source configured to emit light of the green wavelength to the object and a light receiver configured to detect the light scattered or reflected from the object.

The processor may be further configured to extract the DC component of the pulse wave signal using at least one of a band-pass filter or a low pass filter.

The processor may be configured to obtain an intensity at each time point by dividing the DC component of the pulse wave signal of the green wavelength at each time point by the external force at a corresponding time point, and obtain the oscillometric envelope by plotting the intensity of each time point based on the external force at each time point.

The processor may be further configured to determine a peak point in the oscillometric envelope and obtain a feature value for estimating the blood pressure based on the peak point.

The processor may be further configured to obtain the external force at the peak point as a mean arterial pressure (MAP) feature value and estimate the blood pressure based on the MAP feature value.

The processor may be further configured to obtain the external force at a point, that appears before the peak point and corresponds to a first partial value of an intensity of the peak point, as a diastolic blood pressure (DBP) feature value, and estimate the blood pressure based on the DBP feature value.

The processor may be further configured to obtain the external force at a point that appears after the peak point and corresponds to a second partial value of an intensity of the peak point, as a systolic blood pressure (SBP) feature value, and estimate the blood pressure based on the SBP feature value.

According to an aspect of another example embodiment, there is provided a method of estimating blood pressure, the method including: obtaining a pulse wave signal of a green wavelength from an object, by a first sensor when the object is in contact with the first sensor; measuring an external force applied to a second sensor while the pulse wave signal is measured by the first sensor; obtaining an oscillometric envelope based on a direct current (DC) component of the pulse wave signal of the green wavelength and the external force; and estimating the blood pressure using the oscillometric envelope.

The obtaining of the oscillometric envelope may include extracting the DC component of the pulse wave signal using at least one of a band-pass filter or a low pass filter.

The obtaining of the oscillometric envelope may include obtaining an intensity at each time point by dividing the DC component of the pulse wave signal of the green wavelength at each time point by the external force at a corresponding time point, and obtaining the oscillometric envelope by plotting the intensity of each time point based on the external force at each time point.

The estimating of the blood pressure may include determining a peak point in the oscillometric envelope and obtaining a feature value for estimating blood pressure based on the peak point.

The obtaining the feature value may include obtaining the external force at the peak point as a mean arterial pressure (MAP) feature value.

The obtaining of the feature value may include obtaining the external force at a point that appears before the peak point and corresponds to a first preset partial value to an intensity of the peak point, as a diastolic blood pressure (DBP) feature value, and estimating the blood pressure based on the DBP feature value.

The obtaining of the feature value may include the external force at a point that appears after the peak point and corresponds to a second partial value of an intensity of the peak point, as a systolic blood pressure (SBP) feature value, and estimating the blood pressure based on the SBP feature value.

According to an aspect of another example embodiment, there is provided an apparatus for estimating blood pressure, the apparatus including: a first sensor configured to obtain a first pulse wave signal of a green wavelength and a second pulse wave signal of an infrared wavelength from an object when the object is in contact with the first sensor; a second sensor configured to measure an external force exerted onto the second sensor while the first sensor is obtaining the pulse wave signal; and a processor configured to obtain a first oscillometric envelope based on a direct current (DC) component of the first pulse wave signal of the green wavelength and the external force, obtain a second oscillometric envelope based on an alternating current (AC) component of the second pulse wave signal of the infrared wavelength and the external force, and estimate the blood pressure using the first and the second oscillometric envelopes.

The first sensor may include a green light source configured to emit light of the green wavelength to the object, an infrared light source configured to emit light of the infrared wavelength to the object, and a light receiver configured to receive the light of the green wavelength and the light of the infrared wavelength that are scattered or reflected from the object.

The processor may be further configured to obtain an intensity at each time point by dividing the DC component of the first pulse wave signal of the green wavelength at each time point by the external force at a corresponding time point, and obtain the first oscillometric envelope by plotting the intensity of each time point based on the external force at each time point.

The processor may be further configured to determine a first peak point in the first oscillometric envelope and obtain a first feature value based on the first peak point.

The processor may be further configured to determine a second peak point of the second oscillometric envelope, obtain a second feature value for estimating blood pressure based on the second peak point, and estimate the blood pressure based on the first feature value and the second feature value.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
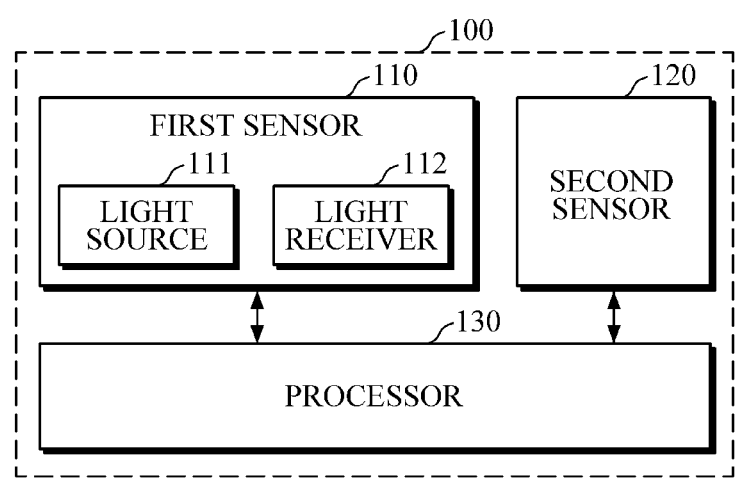
FIG. 1 is a block diagram illustrating an apparatus for estimating blood pressure according to an exemplary embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Various embodiments of an apparatus for estimating blood pressure described hereinafter may be mounted on a terminal, such as a smartphone, a tablet personal computer (PC), a desktop PC, a notebook PC, or the like, or a wearable device. The wearable device may include a wrist watch type, a bracelet type, a wrist band type, a ring type, a glasses type, a hair band type, and the like. However, these are merely examples, and the embodiment is not limited thereto.

FIG. 1 is a block diagram illustrating an apparatus for estimating blood pressure according to an exemplary embodiment.

Referring to FIG. 1, the blood pressure estimation apparatus 100 includes a first sensor 110, a second sensor 120, and a processor 130.

The first sensor 110 measures a photoplethysmography (PPG) signal (hereinafter referred to as a "pulse wave signal") from an object. Here, the object may be a body part which may come into contact with the first sensor 110, or a body part of which pulse waves may be measured by using PPG. For example, the object may be a finger which has a high density of blood vessels, but is not limited thereto, and may be a distal body portion, such as a toe, or the like, or a region of a wrist adjacent to the radial artery or an upper area of the wrist through which capillary blood or venous blood passes.

The first sensor 110 may include a light source 111 configured to emit light of a green wavelength to the object and a light receiver 112 disposed at a predetermined distance apart from the light source 111 and configured to obtain a pulse wave signal of the green wavelength by detecting light scattered or reflected from the object. The light source may include a light emitting diode (LED), a laser diode, and a phosphor, but is not limited thereto. The light receiver may include a photodiode, a photodiode array, a complementary metal-oxide semiconductor (CMOS) image sensor, a charge-coupled device (CCD) image sensor, and the like.

The second sensor 120 may measure a force that is exerted onto the second sensor 120 by the object when the object comes into contact with the first sensor 110 and then increases or decreases the force to induce a change in pulse wave amplitude that is measured by the first sensor 110. Here, the force may correspond to a pressure that is applied by the object against the second sensor 120. The second sensor 120 may include one force sensor formed as a strain gauge or the like, a force sensor array, a pressure sensor, a pressure sensor in the form of an air bladder, a pressure sensor in which a force sensor and an area sensor are combined. For example, the second sensor 120 may be disposed (directly) underneath the first sensor 110, and when the object comes into contact with a contact surface of the first sensor 110 that is exposed to the outside so that the object is able to touch the contact surface of the first sensor 110. When the object exerts a force onto the contact surface of the first sensor 110, the force may be transferred to the second sensor 120 located below the first sensor 110, and the second sensor 120 may measure the force that is transferred from the first sensor 110. The force exerted onto the first sensor 110 may correspond to the force measured by the second sensor 120.

The processor 130 may be electrically connected to the first sensor 110. The processor 130 may control the first sensor 110 and the second sensor 120 to estimate blood pressure, and may receive a pulse wave signal and force/pressure data from the first sensor 110 and the second sensor 120.

The processor 130 may preprocess the pulse wave signal. For example, the processor 130 may remove noise, such as motion noise, using noise removal techniques, such as filtering, smoothing, or the like. For example, when the first signal is an ECG signal, band-pass filtering with a cutoff frequency of 1 Hz to 40 Hz may be performed, and when the first signal is a PPG signal, band-pass filtering with a cutoff frequency of 1 Hz to 10 Hz may be performed.

The processor 130 may acquire an oscillometric envelope based on the received pulse wave signal of the green wavelength and the received force and estimate blood pressure using the acquired oscillometric envelope. However, information to be estimated is not necessarily limited to blood pressure, and it is also possible to estimate vascular age, arterial stiffness, aortic pressure waveform, blood vessel elasticity, stress index, fatigue level, skin age, skin elasticity, and the like.

Hereinafter, an example of acquiring an oscillometric envelope and estimating blood pressure using the oscillometric envelope will be described with reference to FIGS. 2 to 3B.

Figure 2:
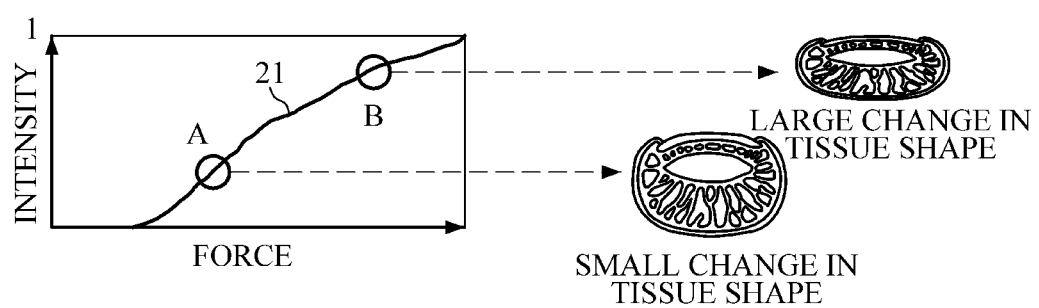
FIG. 2 is a diagram for describing a relationship between a direct current (DC) component of a pulse wave signal of a green wavelength and a tissue change.
Figure 3A:
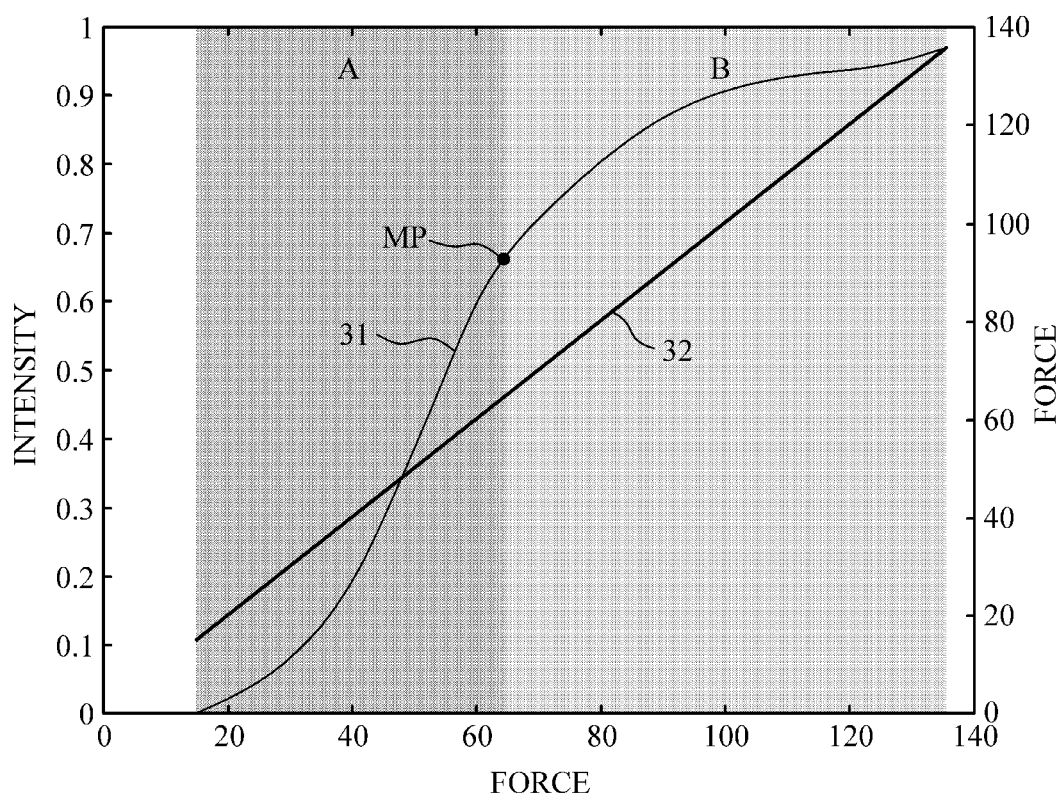
FIGS. 3A and 3B are graphs for describing an example of acquiring an oscillometric envelope using a DC component of a pulse wave signal of a green wavelength.
Figure 3B:
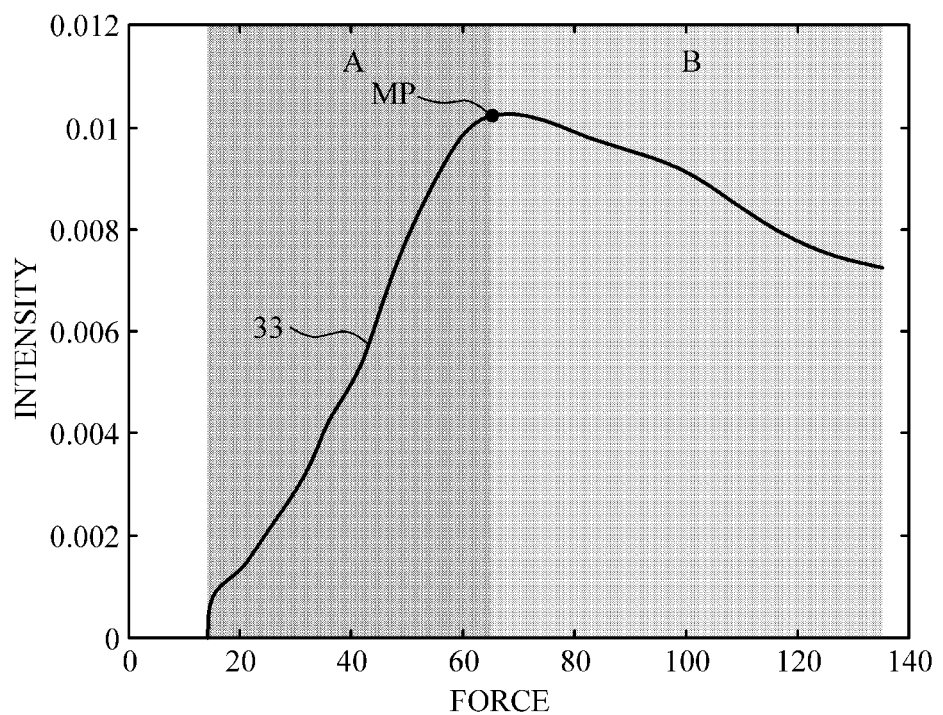

FIG. 2 is a diagram for describing a relationship between a direct current (DC) component of a pulse wave signal of a green wavelength and a tissue change. FIGS. 3A and 3B are graphs for describing an example of acquiring an oscillometric envelope using a DC component of a pulse wave signal of a green wavelength.

In a graph of FIG. 2, the X-axis represents an external force applied by an object to the blood pressure estimation apparatus 100 and Y-axis represents an intensity of a DC component 21 of a normalized pulse wave signal of a green wavelength. The DC component 21 of the pulse wave signal of the green wavelength rises as the force applied to the subject increases, which shows that there is a certain correlation with the change in tissue or blood vessels of the object. That is, it can be seen that the tissue shape change at the point A where the DC component 21 is relatively low is small and the tissue shape change at the point B where the DC component 21 is relatively high is large. As such, it can be seen that the DC component 21 of the pulse wave signal of the green wavelength is a signal that corresponds to the amount of blood in the blood vessel. Thus, it is possible to estimate blood pressure using the DC component 21 of the pulse wave signal of the green wavelength and the force and thus to increase accuracy of blood pressure estimation using the pulse wave signal of the green wavelength relatively robust to motion noise or the like.

When the pulse wave signal of the green wavelength is received from the first sensor 110, the processor 130 may extract a DC component of the received pulse wave signal. For example, the processor 130 may extract the DC component of the pulse wave signal using a band-pass filter, a low pass filter, or the like. Also, a DC component value at time point may be normalized to have a value within a range of 0 to 1 by dividing the extracted DC component value at each time point by the maximum value of the DC component.

FIG. 3A is a graph showing a DC component 31 of a pulse wave signal of a green wavelength and a force 32. As an object increases a pressing force, tissues and blood vessels are gradually pressed in specific section A, and tissue deformation occurs, without the change in size of the blood vessel, in section B after a specific time point MP, for example, a time point at which the force applied and the mean arterial pressure MAP become the same.

The processor 130 may obtain an oscillometric envelope using a force 32 at a corresponding time point of the DC component 31 of the normalized pulse wave signal of the green wavelength. For example, the processor 130 may obtain the intensity of each time point, e.g., the amount of blood per unit force, by dividing a DC component 31 of a pulse wave signal of a green wavelength at each time point by the force 32 at the corresponding time point, and obtain an oscillometric envelope 33 by plotting the obtained intensity based on the force at each time point as shown in FIG. 3B. It can be seen from the oscillometric envelope 33 that the amount of blood per unit force gradually increases in section A and gradually decreases in section B after the specific time point MP.

The processor 130 may determine a characteristic point from the thus obtained oscillometric envelope 33 and obtain feature values for blood pressure estimation, such as force and/or intensity of the characteristic point. For example, referring to FIG. 3B, the processor 130 may detect a peak point MP from the oscillometric envelope 33 and obtain force at the detected peak point as an MAP feature value. Also, the processor 130 may obtain force and/or intensity at a point, corresponding to a first preset partial value or a partial percentage value (e.g., 0.5 to 0.7, or 50% to 70%) of the intensity of the peak point MP, in a section A before the peak point MP as a diastolic blood pressure (DBP) feature value. In addition, the processor 130 may obtain a force and/or intensity at a point, corresponding to a second preset partial value or a partial percentage value (0.5 to 0.7) of the intensity of the peak point MP, in a section B after the peak point MP as a systolic blood pressure (SBP) feature value.

The processor 130 may estimate blood pressure by applying the obtained feature values to a blood pressure estimation model. Equation 1 below illustrates a blood pressure estimation model defined as a simple linear combination function. However, the blood pressure estimation model is not limited to the linear combination function, and may be predefined in various ways, such as linear/nonlinear regression analysis, neural network, deep learning, and the like.

$$y=ax+b \quad \text{[Equation 1]}$$

Here, y represents an estimated blood pressure value, x represents a feature value, a represents a predefined adjustment coefficient of a feature value, and b represents an offset and may be, for example, a cuff blood pressure obtained at the time of calibration. Here, a and/or b may be defined for each of MAP, DBP, and SBP, and MAP, DBP, and SBP may be independently estimated by applying the MAP feature value, the DBP feature value, the SBP feature value to each blood pressure estimation model.

Figure 4:
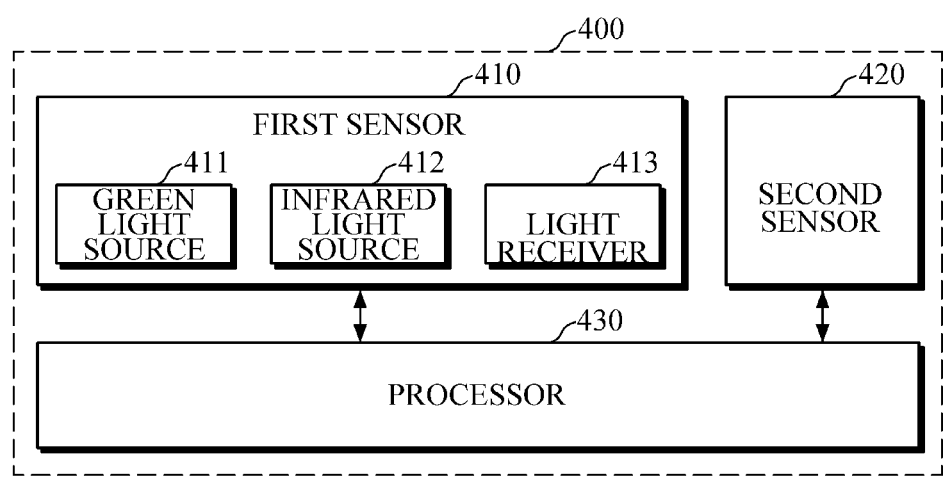
FIG. 4 is a block diagram illustrating an apparatus for estimating blood pressure according to another exemplary embodiment.
Figure 5A:
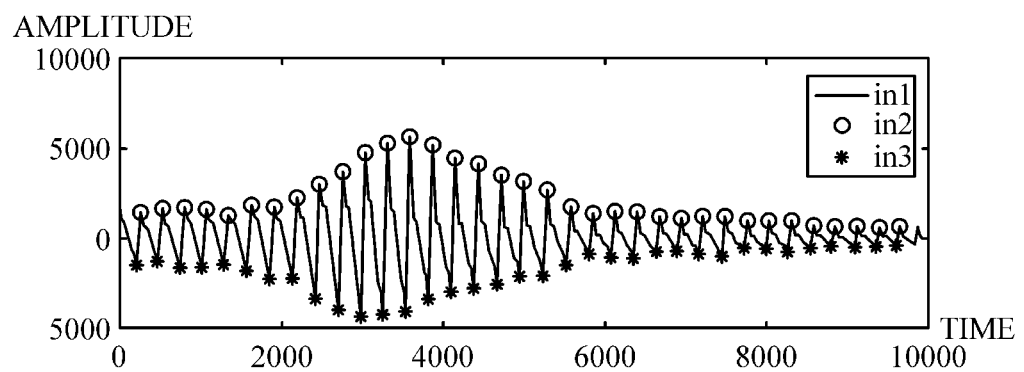
FIGS. 5A to 5C are graphs for describing an example of acquiring an oscillometric envelope using a pulse wave signal of an infrared wavelength.
Figure 5B:
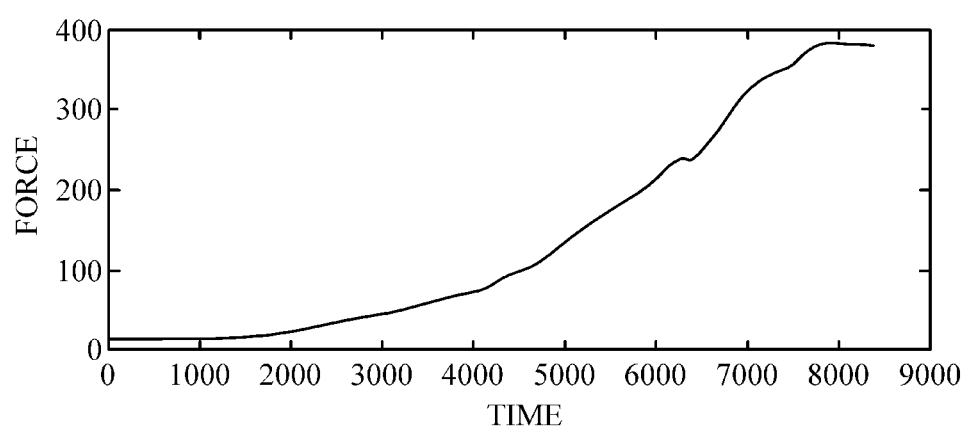
Figure 5C:
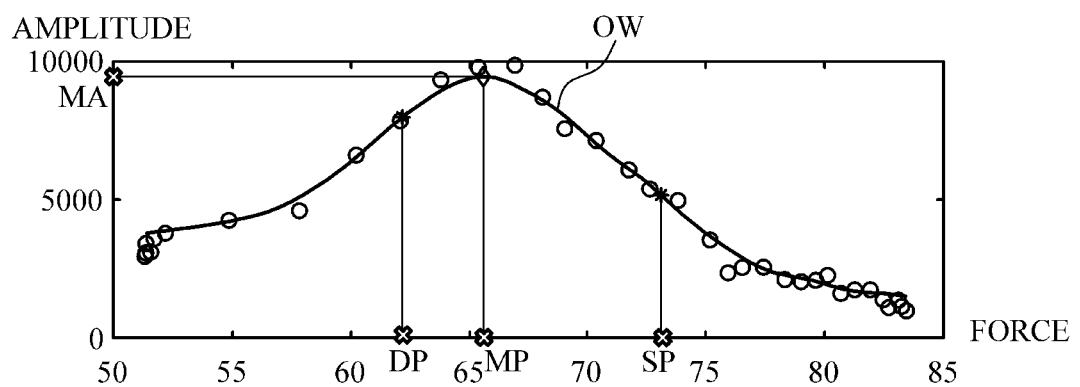

FIG. 4 is a block diagram illustrating an apparatus for estimating blood pressure according to another exemplary embodiment. FIGS. 5A to 5C are graphs for describing an example of acquiring an oscillometric envelope using a pulse wave signal of an infrared wavelength.

Referring to FIG. 4, an apparatus 400 for estimating blood pressure may include a first sensor 410, a second sensor 420, and a processor 430.

The first sensor 410 may measure a pulse wave signal of a green wavelength and a pulse wave signal of an infrared wavelength from an object. The first sensor 410 may include a green light source 411 configured to emit light of a green wavelength to the object and an infrared light source 412 configured to emit light of an infrared wavelength. In addition, the first sensor 410 may include one or more light receivers 413 configured to detect light scattered or reflected from the object and obtain the pulse wave signal of the green wavelength and the pulse wave signal of the infrared wavelength. The light sources 411 and 412 may include LEDs, laser diodes, and phosphors, and the light receiver 413 may include a photodiode, a photodiode array, a CMOS image sensor, a CCD image sensor, and the like.

The second sensor 420 may measure an external force that is exerted onto the second sensor 420 (e.g., a force exerted on the second sensor 420 by a finger) when the object is in contact with the first sensor 410 and increases or decreases pressing force to induce a change in pulse wave amplitude. The second sensor 420 may include one force sensor formed as a strain gauge or the like, a force sensor array, a pressure sensor, a pressure sensor in the form of an air bladder, a pressure sensor in which a force sensor and an area sensor are combined.

The processor 430 may receive a pulse wave signal and force data from the first sensor 410 and the second sensor 420, and preprocess the received pulse wave signals of green wavelength and infrared wavelength.

The processor 430 may estimate blood pressure using the received pulse wave signals of green wavelength and infrared wavelength and the received force.

For example, the processor 430 may extract a DC component by preprocessing the pulse wave signal of the green wavelength as described above, normalize the extracted DC component, and obtain a first oscillometric envelope using the normalized DC component and the force. The processor 430 may obtain an MAP feature value, a DBP feature value, and/or an SBP feature value from the obtained first oscillometric envelope.

In addition, the processor 430 may preprocess the pulse wave signal of the infrared wavelength and obtain a second oscillometric envelope using an alternating current (AC) component of the pulse wave signal of the infrared wavelength and a force.

FIG. 5A shows an AC component of a pulse wave signal of an infrared wavelength, FIG. 5B shows a force, and FIG. 5C shows an oscillometric envelope obtained using the AC component of the pulse wave signal of the infrared wavelength and the force.

For example, referring to FIGS. 5A to 5C, the processor 430 may extract a peak-to-peak point by subtracting an amplitude value at a negative (−) point, e.g., a foot amplitude value in3, from an amplitude value at a positive (+) point of a pulse wave envelope in1 at each measurement point, e.g., a peak amplitude value in2, plot the amplitude of the peak-to-peak point based on the force corresponding to each time point, and obtain the second oscillometric envelope OW by performing, for example, polynomial curve fitting.

The processor 430 may obtain feature values from the second oscillometric envelope OW acquired from the pulse wave signal of the infrared wavelength. For example, as illustrated, a force MP of an amplitude maximum point of the second oscillometric envelope OW may be obtained as an MAP feature value. In addition, force DP and SP, at each of which an amplitude has a value equal to a predetermined partial value or a partial percentage value (e.g., 0.5 to 0.7, or 50% to 70%) of the maximum amplitude value MA, may be obtained as a DBP feature value and an SBP feature value, respectively.

The processor 430 may estimate blood pressure using the MAP feature values, the DBP feature values, and the SBP feature values obtained from each of the first oscillometric envelope and the second envelope. For example, a combination (e.g., mean) of the MAP feature values obtained from each oscillometric envelope, a combination (e.g., mean) of the DBP feature values, and a combination (e.g., mean) of the SBP feature values may be input to the blood pressure estimation model to estimate MAP, DBP, and SBP.

Figure 6:
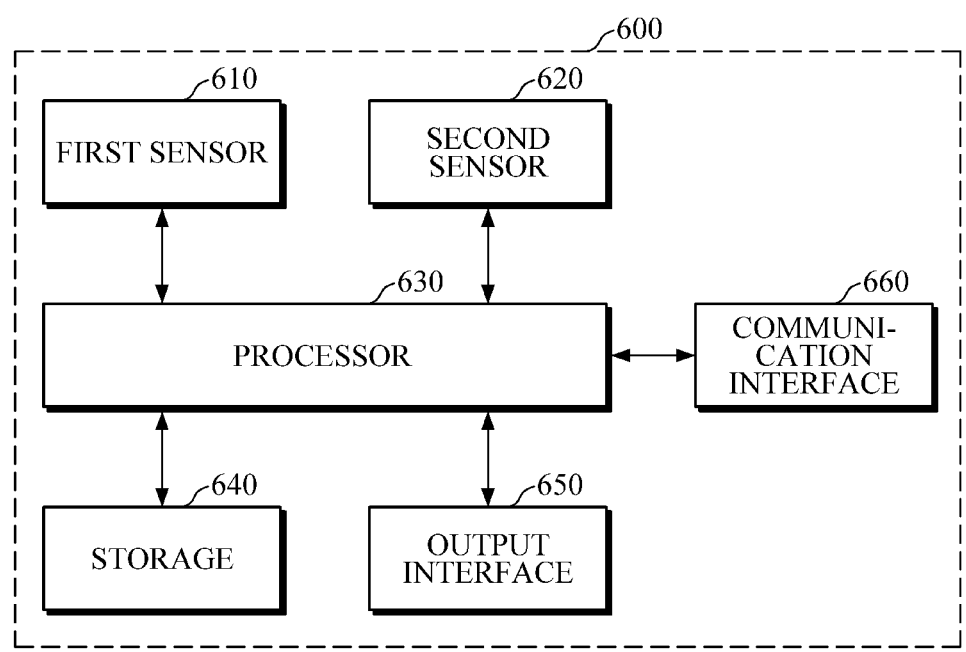
FIG. 6 is a block diagram illustrating an apparatus for estimating blood pressure according to still another exemplary embodiment.

FIG. 6 is a block diagram illustrating an apparatus for estimating blood pressure according to still another exemplary embodiment.

Referring to FIG. 6, an apparatus 600 for estimating blood pressure may include a first sensor 610, a second sensor 620, a processor 630, a storage 640, an output interface 650, and a communication interface 660. The first sensor 610, the second sensor 620, and the processor 630 are described above and hence detailed descriptions thereof will be omitted below.

Data related to blood pressure estimation is stored in the storage 640. For example, a pulse wave signal, force, an oscillometric envelope, feature values, estimated blood pressure values, and the like, which are measured and processed by the first sensor 610, the second sensor, 620 and the processor 630, may be stored in the storage 640. In addition, user's characteristic information, such as user's gender, age, and health condition, and data on reference blood pressure, a blood pressure estimation model, and the like may be stored. However, the information and data to be stored are not limited to the above examples.

The storage 640 may include at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk.

The output interface 650 may output data related to blood pressure estimation. For example, the output interface 650 may output a pulse wave signal, force, an oscillometric envelope, feature values, estimated blood pressure values, and the like, which are measured and processed by the first sensor 610, the second sensor, 620 and the processor 630. The output interface 650 may output data to the user through various visual/non-visual methods using a display, a sound output module, a haptic module, and the like.

The communication module 660 may communicate with an external device under the control of the processor 630 to transmit and receive various data using wired/wireless communication technologies. For example, the communication interface 660 may transmit a blood pressure estimation result to the external device and receive various types of reference information required for blood pressure estimation from the external device. In this case, the external device may include an information processing device, such as a cuff-type blood pressure measurement device, a smartphone, a tablet PC, a desktop PC, a notebook PC, and the like.

In this case, the communication technology may Bluetooth communication, Bluetooth low energy (BLE) communication, near field communication (NFC), wireless local access network (WLAN) communication, ZigBee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, and/or 5G communication. However, these are merely examples, and the embodiment is not limited thereto.

Figure 7:
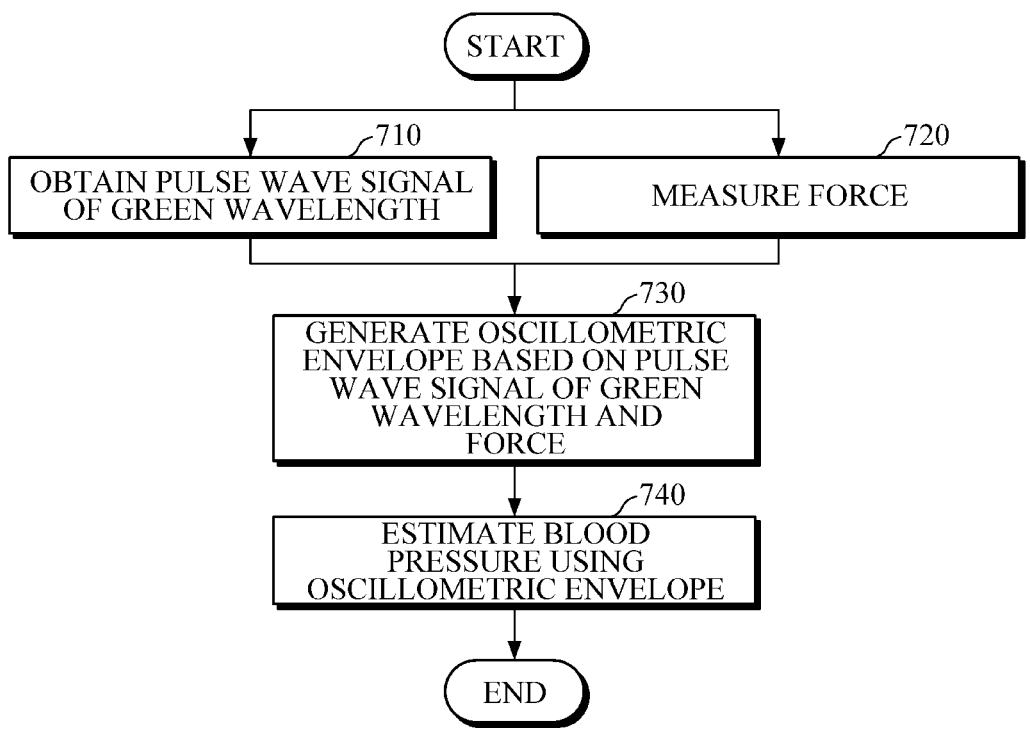
FIG. 7 is a flowchart illustrating a method of estimating blood pressure according to an exemplary embodiment.

FIG. 7 is a flowchart illustrating a method of estimating blood pressure according to an exemplary embodiment.

The method of FIG. 7 may be one exemplary embodiment of a blood pressure estimating method performed by the apparatus for estimating blood pressure according to the embodiment of FIG. 1 or 6. Hereinafter, the method will be described in brief to avoid redundancy.

First, the apparatus for estimating blood pressure may obtain a pulse wave signal of a green wavelength from an object by using a first sensor when the object is in contact with the first sensor in operation 710.

In addition, the apparatus may measure a force applied by the object in contact with the first sensor by using a second sensor in operation 720.

Then, an oscillometric envelope may be obtained based on the pulse wave signal of the green wavelength and the force in operation 730. For example, the apparatus may extract a DC component of the pulse wave signal of the green wavelength and normalize the DC component, and divide the normalized DC component by the force to obtain the oscillometric envelope.

Then, blood pressure may be estimated using the oscillometric envelope in operation 740. For example, an MAP feature value, a DBP feature value, and an SBP feature value are obtained based on a characteristic point, for example, a peak point, from the oscillometric envelope and blood pressure may be estimated using the obtained feature values.

Figure 8:
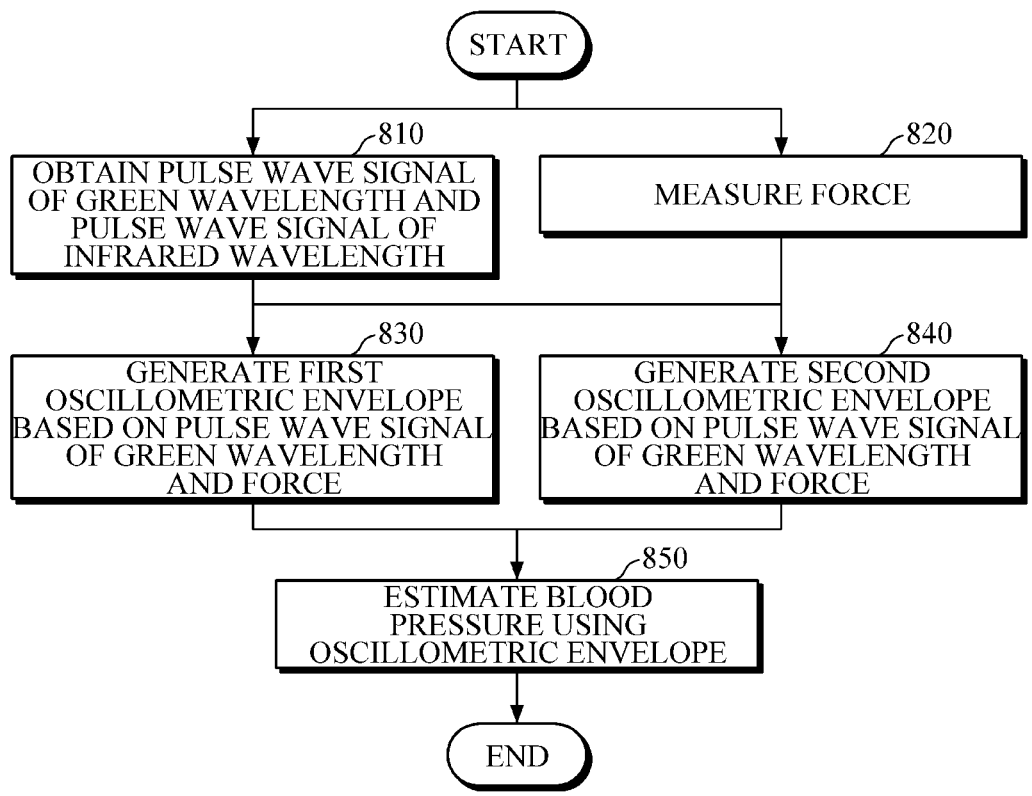
FIG. 8 is a flowchart illustrating a method of estimating blood pressure according to another exemplary embodiment.

FIG. 8 is a flowchart illustrating a method of estimating blood pressure according to another exemplary embodiment.

The method of FIG. 8 may be one exemplary embodiment of a blood pressure estimating method performed by the apparatus for estimating blood pressure according to the embodiment of FIG. 4 or 6. Hereinafter, the method will be described in brief to avoid redundancy.

First, the apparatus for estimating blood pressure may obtain a pulse wave signal of a green wavelength and a pulse wave signal of an infrared wavelength from an object using a first sensor when the object is in contact with the first sensor in operation 810.

In addition, the apparatus may measure a force applied by the object in contact with the first sensor by using a second sensor in operation 820.

Then, a first oscillometric envelope may be obtained based on the pulse wave signal of the green wavelength and the force in operation 830. For example, the apparatus may extract a DC component of the pulse wave signal of the green wavelength and normalize the DC component, and divide the normalized DC component by the force to obtain the oscillometric envelope.

In addition, the apparatus may obtain a second oscillometric envelope based on the pulse wave signal of the infrared wavelength and the force in operation 840. For example, the second oscillometric envelope may be obtained using a peak and foot of an AC component of the pulse wave signal of the infrared wavelength and the force.

Then, blood pressure may be estimated using the first oscillometric envelope and the second oscillometric envelope in operation 850. For example, first feature values, for example, an MAP feature value, a DBP feature value, and an SBP feature value, may be obtained based on a peak point of the first oscillometric envelope, and second feature values, for example, an MAP feature value, a DBP feature value, and an SBP feature value, may be obtained based on a peak point of the second oscillometric envelope. In addition, the obtained first feature values and second feature values may be combined and blood pressure may be estimated using a blood pressure estimation model.

Figure 9:
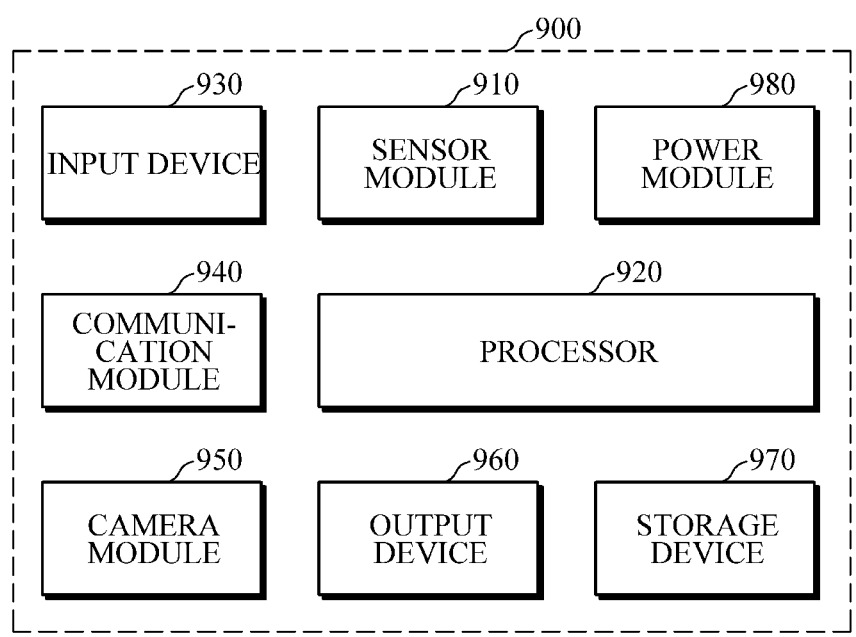
FIG. 9 is a block diagram illustrating an example of an electronic device including an apparatus for estimating blood pressure.
Figure 10:
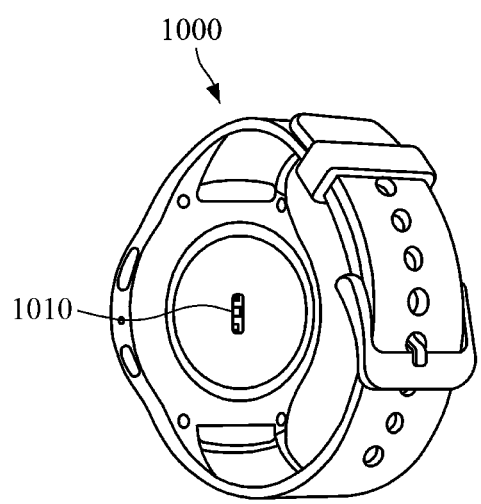
FIG. 10 is a diagram illustrating a watch-type embodiment of the electronic device of FIG. 9.
Figure 11:
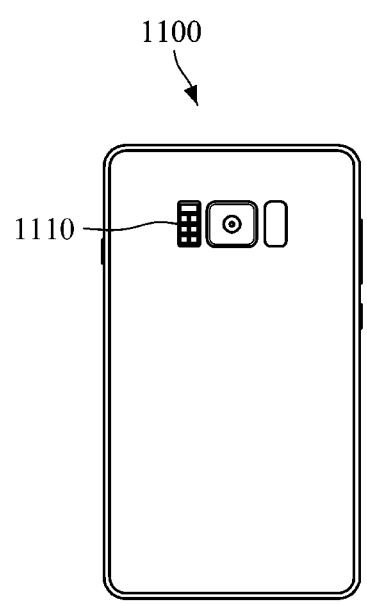
FIG. 11 is a diagram illustrating a mobile-type embodiment of the electronic device of FIG. 9.
Figure 12:
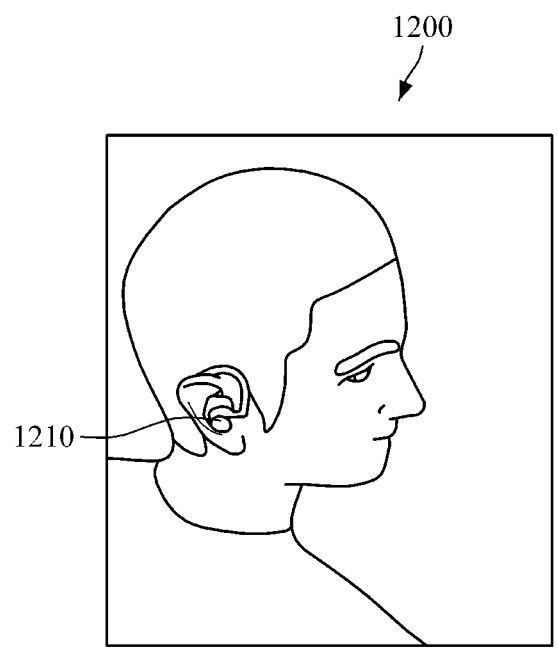
FIG. 12 is a diagram illustrating an ear-wearable-type embodiment of the electronic device of FIG. 9.

FIG. 9 is a block diagram illustrating an example of an electronic device including an apparatus for estimating blood pressure. FIG. 10 is a diagram illustrating a watch-type embodiment of the electronic device of FIG. 9. FIG. 11 is a diagram illustrating a mobile-type embodiment of the electronic device of FIG. 9. FIG. 12 is a diagram illustrating an ear-wearable-type embodiment of the electronic device of FIG. 9.

Referring to FIG. 9, an electronic device 900 may include a sensor module 910, a processor 920, an input device 930, a communication module (e.g., a communication interface) 940, a camera module (e.g., a camera) 950, an output device 960, a storage device 970, and a power module (e.g., a power supply) 980. The components of the electronic device 900 may be integrally mounted in a specific device, or mounted in two or more devices in a distributed manner.

The sensor module 910 may include the first sensor and the second sensor of the apparatus 100, 400, or 600 for estimating blood pressure described above. The first sensor may include a light source and a light receiver. In this case, the light source may be formed as a light source of a green wavelength alone or a light source of a green wavelength and a light source of an infrared wavelength according to the above-described embodiments of the apparatus for estimating blood pressure. The first sensor may obtain a pulse wave signal of a green wavelength and/or a pulse wave signal of an infrared wavelength when an object is in contact with the first sensor. The second sensor may be disposed above or below the first sensor and measure a force that acts between the object and the first sensor. The sensor module 910 may include various sensors for performing other functions, for example, a gyro sensor, a global positioning system (GPS) sensor, and the like.

The processor 920 may control the components connected to the processor 920 by executing a program or the like stored in the storage device 970, and may perform various data processing or operations. The processor 920 may include a main processor, such as a central processing unit and an application processor, and a co-processor that can be operated independently or together with the main processor, for example, a graphics processing unit, an image signal processor, a sensor hub processor, a communication processor, and the like.

The processor 920 may transmit a control signal to the sensor module 910 in response to a user's request for estimating blood pressure, and may estimate blood pressure in the above-described manner using the pulse wave signal and force received from the sensor module 910.

The input device 930 may receive a command and/or data to be used in each component of the electronic device 900 from the user or the like. The input device 930 may include a microphone, a mouse, a keyboard, and/or a digital pen (a stylus pen, etc.).

The communication module 940 may support the establishment of a direct (cable) communication channel and/or wireless communication channel between the electronic device 900 and another electronic device or server in a network environment or the sensor module 910 and the communication therebetween through the established communication channel. The communication module 940 may be operated independently of the processor 920 and may include one or more communication processors that support direct communication and/or wireless communication. The communication module 940 may include a wireless communication module, such as, a cellular communication module, a short-range wireless communication module, a global navigation satellite system (GNSS) communication module, or the like, and/or a wired communication module, such as a local area network (LAN) communication module, a power line communication module, or the like. Such various types of communication modules may be integrated into a single chip, or may be implemented as a plurality of separate chips. The wireless communication module may verify and authenticate the electronic device 900 in a communication network using subscriber information (e.g., international mobile subscriber identity (IMSI), or the like) stored in a subscriber identity module.

The camera module 950 may capture still images and moving images. The camera module 950 may include a lens assembly including one or more lenses, image sensors, image signal processors, and/or flashes. The lens assembly included in the camera module may collect light emitted from a subject to be imaged.

The output device 960 may output data generated or processed by the electronic device 900 in a visual/non-visual manner. The output device 960 may include a sound output device, a display device, an audio module, and/or a haptic module.

The sound output device may output a sound signal to the outside of the electronic device 900. The sound output device may include a speaker and/or a receiver. The speaker may be used for general purposes, such as multimedia playback or recording playback, and the receiver may be used to incoming calls. The receiver may be combined as part of the speaker or may be implemented as an independent separate device.

The display device may visually provide information to the outside of the electronic device 900. The display device may include a display, a hologram device, or a projector, and a control circuit for controlling the device. The display device may include touch circuitry set to sense touch and/or sensor circuitry (a pressure sensor, etc.) set to measure the intensity of force generated by the touch.

The audio module may convert sound into an electric signal or inversely convert an electric signal into sound. The audio module may obtain sound through the input device, and may output sound through the sound output device and/or a speaker and/or a headphone of another electronic device directly or wirelessly connected to the electronic device 900.

The haptic module may convert an electrical signal into a mechanical stimulus (e.g., a vibration or a movement) or electrical stimulus which may be recognized by a user via his tactile sensation or kinesthetic sensation. The haptic module may include a motor, a piezoelectric element, and/or an electric stimulator.

The storage device 970 may store driving conditions required for driving the sensor module 910 and various data required by other components of the electronic device 900, for example, software and input data and/or output data for commands related to the software. The storage device 970 may include volatile memory and/or non-volatile memory.

The power module 980 may manage power supplied to the electronic device 900. The power module may be configured as part of a power management integrated circuit (PMIC). The power module 980 may include a battery and the battery may include a non-rechargeable primary cell, a rechargeable secondary cell, and/or a fuel cell.

FIGS. 10 to 12 are diagrams illustrating structures of the electronic device 900 of FIG. 9 by way of example.

Referring to FIG. 10, the electronic device 900 may be configured as a watch-type wearable device 1000 and may include a main body and a strap. A display may be provided on the front surface of the main body to display various application screens containing time information, received message information, etc. A sensor module 1010 may be disposed on a rear surface of the main body to measure a pulse wave signal and force for blood pressure estimation.

Referring to FIG. 11, the electronic device 900 may be configured as a mobile device 1100, such as a smart phone.

The mobile device 1100 may include a housing and a display panel. The housing may form the outer appearance of the mobile device 1100. The display panel and cover glass may be sequentially arranged on a first surface of the main body, and the display panel may be exposed to the outside through the cover glass. A sensor module 1110, a camera module, and/or an infrared sensor may be disposed on a second surface of the main body. When a user requests estimation of biological information by executing an application installed in the mobile device 1100, blood pressure may be estimated using the sensor module 1110 and the estimated blood pressure value may be provided to the user as an image and/or sound.

Referring to FIG. 12, the electronic device 900 may also be configured as an ear wearable device 1200.

The ear wearable device 1200 may include a main body and an ear strap. The user may wear the electronic device by wearing the ear strap on the auricle. The ear strap may be omitted depending on the shape of the ear wearable device 1200. The main body may be inserted into the external auditory meatus of the user. A sensor module 1210 may be mounted in the main body. The ear wearable device 1200 may provide a blood pressure estimation result to the user as sound, or may transmit the blood pressure estimation result to an external device, such as a mobile device, a tablet PC, or the like, through a communication module provided in the main body.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating blood pressure, comprising:
    a first sensor configured to obtain a pulse wave signal of a green wavelength and a pulse wave signal of an infrared wavelength from an object when the object is in contact with the first sensor;
    a second sensor configured to measure an external force applied to the second sensor while the first sensor is obtaining the pulse wave signal of the green wavelength and the pulse wave signal of the infrared wavelength; and
    a processor configured to:
        obtain a direct current (DC) component of the pulse wave signal of the green wavelength as a green PPG DC signal;
        identify a change in the green PPG DC signal as the external force increases over time;
        obtain a first oscillometric envelope representing a blood amount in a blood vessel per unit force by dividing the green PPG DC signal by the external force;
        obtain a second oscillometric envelope based on the pulse wave signal of the infrared wavelength and the external force measured by the second sensor;
        obtain a first mean arterial pressure (MAP) feature value, a first diastolic blood pressure (DBP) feature value, and a first systolic blood pressure (SBP) feature value based on a peak value of the first oscillometric envelope;
        obtain a second MAP feature value, a second DBP feature value, and a second SBP feature value based on a peak value of the second oscillometric envelope; and
        estimate the blood pressure based on a combination of the first MAP feature value and the second MAP feature value, a combination of the first DBP feature value and the second DBP feature value, and a combination of the first SBP feature value and the second SBP feature value; and
    a display configured to output the estimated blood pressure.

2. The apparatus of claim 1, wherein the processor is further configured to extract the DC component of the pulse wave signal of the green wavelength using a band-pass filter with a cutoff frequency range from 1 Hz to 10 Hz.

3. The apparatus of claim 1, wherein the processor is further configured to determine a peak point in the first oscillometric envelope and obtain a feature value for estimating the blood pressure based on the peak point.

4. The apparatus of claim 3, wherein the processor is further configured to obtain the external force at the peak point as the first MAP feature value, and estimate the blood pressure based on a predetermined percentage value of the first MAP feature value, wherein the predetermined percentage value is in a range from 50% to 70%.

5. The apparatus of claim 3, wherein the processor is further configured to obtain the external force at a point, that appears before the peak point and corresponds to a first partial value of an intensity of the peak point, as the first DBP feature value.

6. The apparatus of claim 3, wherein the processor is further configured to obtain the external force at a point that appears after the peak point and corresponds to a second partial value of an intensity of the peak point, as the first SBP feature value.

7. A method of estimating blood pressure, the method comprising:
    obtaining a pulse wave signal of a green wavelength and obtaining a pulse wave signal of an infrared wavelength from an object, by a first sensor when the object is in contact with the first sensor;
    measuring an external force applied to a second sensor while the pulse wave signal of the green wavelength and the pulse wave signal of the infrared wavelength are measured by the first sensor;
    obtaining a direct current (DC) component of the pulse wave signal of the green wavelength as a green PPG DC signal;
    identifying a change in the green PPG DC signal as the external force increases over time; and
    obtaining a first oscillometric envelope representing a blood amount in a blood vessel per unit force by dividing the green PPG DC signal by the external force;
    obtaining a second oscillometric envelope based on the pulse wave signal of the infrared wavelength and the external force measured by the second sensor;
    obtaining a first mean arterial pressure (MAP) feature value, a first diastolic blood pressure (DBP) feature value, and a first systolic blood pressure (SBP) feature value based on a peak value of the first oscillometric envelope;

obtaining a second MAP feature value, a second DBP feature value, and a second SBP feature value based on a peak value of the second oscillometric envelope; and estimating the blood pressure based on a combination of the first MAP feature value and the second MAP feature value, a combination of the first DBP feature value and the second DBP feature value, and a combination of the first SBP feature value and the second SBP feature value.

8. The method of claim 7, wherein the obtaining of the first oscillometric envelope comprises extracting the DC component of the pulse wave signal of the green wavelength using at least one of a band-pass filter or a low pass filter.

9. The method of claim 7, wherein the estimating of the blood pressure comprises determining a peak point in the first oscillometric envelope and obtaining a feature value for estimating blood pressure based on the peak point.

10. The method of claim 9, wherein the obtaining the feature value comprises obtaining the external force at the peak point as the first MAP feature value.

11. The method of claim 9, wherein the obtaining of the feature value comprises obtaining the external force at a point that appears before the peak point and corresponds to a first preset partial value to an intensity of the peak point, as the first DBP feature value.

12. The method of claim 9, wherein the obtaining of the feature value comprises obtaining the external force at a point that appears after the peak point and corresponds to a second partial value of an intensity of the peak point, as the first SBP feature value.

* * * * *